United States Patent
Oshmyansky et al.

(10) Patent No.: US 10,240,361 B2
(45) Date of Patent: Mar. 26, 2019

(54) APPARATUS FOR DISPENSING SANITIZER FLUID AND RECORDING DATA PERTAINING TO HAND SANITIZATION

(71) Applicant: Altitude Medical, Inc., Boston, MA (US)

(72) Inventors: Alexander Roman Oshmyansky, Baltimore, MD (US); Jacob Vincent McKnight, Dunoon (GB); Richard James Gilbert, London (GB); Adam Wilmore Paterson, Dolphinton (GB); Matthew David Laws, London (GB)

(73) Assignee: Altitude Medical, Inc., Boston, MA (US)

( * ) Notice: Subject to any disclaimer, the term of this patent is extended or adjusted under 35 U.S.C. 154(b) by 0 days.

(21) Appl. No.: 15/597,585

(22) Filed: May 17, 2017

(65) Prior Publication Data

US 2017/0254111 A1    Sep. 7, 2017

Related U.S. Application Data

(63) Continuation of application No. 14/424,150, filed as application No. PCT/US2013/053586 on Aug. 5, 2013, now Pat. No. 9,670,692.
(Continued)

(51) Int. Cl.
| | |
|---|---|
| *B67D 7/84* | (2010.01) |
| *E05B 1/00* | (2006.01) |
| *G08B 21/24* | (2006.01) |
| *A61L 2/00* | (2006.01) |
| *A61L 2/18* | (2006.01) |

(Continued)

(52) U.S. Cl.
CPC ............ *E05B 1/0069* (2013.01); *A47B 95/02* (2013.01); *A47K 5/1202* (2013.01); *A61L 2/0088* (2013.01); *A61L 2/18* (2013.01); *A61L 2/24* (2013.01); *B05B 11/3052* (2013.01); *E05B 1/0084* (2013.01); *G07C 9/00896* (2013.01); *G08B 21/245* (2013.01); *A47B 2220/0047* (2013.01); *A47K 5/12* (2013.01); *A61L 2202/14* (2013.01); *A61L 2202/15* (2013.01); *B67D 1/00* (2013.01); *B67D 7/84* (2013.01); *E05B 1/0015* (2013.01); *G04C 23/42* (2013.01); *G07C 9/00158* (2013.01); *G07C 2209/65* (2013.01)

(58) Field of Classification Search
CPC ....... A47K 5/12; A47K 5/1202; A61L 2/0088; A61L 2/18; A61L 2/24; A61L 2202/14; A61L 2202/15; G07C 9/00158; G07C 9/00896; G07C 2209/65; G04C 23/42; E05B 1/0069; E05B 1/0015; E05B 1/0084; A47B 95/02; A47B 2220/0047; B67D 7/84; B67D 1/00; B05B 11/3052; G08B 21/245

See application file for complete search history.

(56) References Cited

U.S. PATENT DOCUMENTS 6,553,779 B1 * 4/2003 Boyer .................... A23G 9/045
                                                      222/146.6
8,299,896 B2 * 10/2012 Mahmoodi .............. G07C 1/10
                                                      340/5.82

(Continued)

*Primary Examiner* — Frederick C Nicolas
(74) *Attorney, Agent, or Firm* — Moser Taboada

(57) ABSTRACT

Apparati and methods for dispensing sanitizer fluid via handles on doors and equipment, and data and recording events pertaining to hand sanitization, are disclosed.

20 Claims, 8 Drawing Sheets

Related U.S. Application Data

(60) Provisional application No. 61/693,827, filed on Aug. 28, 2012, provisional application No. 61/693,870, filed on Aug. 28, 2012.

(51) Int. Cl.

| | | |
|---|---|---|
| *A61L 2/24* | (2006.01) | |
| *A47B 95/02* | (2006.01) | |
| *G07C 9/00* | (2006.01) | |
| *A47K 5/12* | (2006.01) | |
| *B67D 1/00* | (2006.01) | |
| *G04C 23/42* | (2006.01) | |
| *B05B 11/00* | (2006.01) | |

(56) References Cited

U.S. PATENT DOCUMENTS

| | | |
|---|---|---|
| 2006/0153733 A1 | 7/2006 | Sassoon |
| 2006/0231568 A1* | 10/2006 | Lynn .................. A47K 5/1202 222/52 |
| 2007/0229288 A1 | 10/2007 | Ogrin et al. |
| 2009/0265990 A1 | 10/2009 | Stratmann |
| 2012/0187146 A1 | 7/2012 | Chopra |

* cited by examiner

APPARATUS FOR DISPENSING SANITIZER FLUID AND RECORDING DATA PERTAINING TO HAND SANITIZATION

CROSS-REFERENCE TO RELATED APPLICATIONS

This application is a continuation of co-pending U.S. patent application Ser. No. 14/424,150 filed Feb. 26, 2015, which is a 371 of International Application Serial No. PCT/US2013/053586 filed Aug. 5, 2013, which claims benefit of U.S. Provisional Patent Application Ser. No. 61/693,827 filed Aug. 28, 2012 and U.S. Provisional Patent Application Ser. No. 61/693,870 filed Aug. 28, 2012, all of which are incorporated herein by reference in their entireties.

BACKGROUND

Field of the Invention

Embodiments of the present invention generally relate to health care technology and, in particular, to methods and apparati for promoting hand sanitization via handles.

Description of the Related Art

Prevention of harmful diseases is a major concern for governments as well as various enterprises, such as companies, corporations, multi-national corporations, and other institutions in which many people are present. In particular, health care facilities, such as hospitals, will be overrun with patients during epidemics. Furthermore, the available medical professional force will be strained and, moreover, infections may be spread by medical personnel and visitors in these very health care facilities. In order to ensure a productive work and living environment, various enterprises and governments use various health care technologies, such as sanitizer fluids, to stop the spread of pathogens that cause the harmful diseases, although past attempts at solving the spread of infectious diseases have been limited. Similarly, medics and health workers have struggled to obtain exact and timely information pertaining to rates of hand sanitization in different areas of the hospital. This information assists health workers in targeting interventions.

Therefore, there is a need in the art for a method and apparatus for dispensing sanitizer fluid via handles, such as handles attached to doors attached to medical equipment, such as ovens, autoclaves, refrigerators, and the like, as well as doors for access to, for example, operating rooms, delivery rooms, patient examination rooms, restrooms, and the like, that prevents nosocomial infections as well as infections occurring at schools, universities, corporations, stores, and the like, and, additionally provides feedback on usage of hand sanitizer and/or is designed so that the dispensation of sanitizer fluid does not spill onto the floor but instead into the palm of the hand and/or is easy to use and apply but, if required, the user can bypass its use when, for example, opening a door.

SUMMARY

Embodiments of the present invention include a method and apparatus for sanitizing the hand using a sanitizer-dispensing door handle that also features electronics which monitor both when the handle is used to open a door, and also whether and when sanitizer is dispensed. The apparatus comprises: a metal or plastic body; a cartridge designed so as to fit within the body of the handle; an access door which allows the cartridge to be fitted within the handle; a cartridge formed of a collapsible shell, and a collapsible pump filled with hand sanitizer; and a compressible trigger piece that compresses the collapsible pump and releases hand sanitizer. The apparatus also comprises an electronic circuit(s) that senses and records the presence of the hand on the handle and when the dispenser is triggered. The sensing circuit(s) is comprised of, for example, a conductive material that emits an electrical field; a pressure switch coupled to the trigger of the dispensing apparatus; and a control circuit that both records and collates the data and is able to transmit this data wirelessly. Manipulation of the handle is recorded as a 'door opening event' and operation of the handle is recorded as a 'hand sanitization event'. The data can be retrieved from the control circuit by holding a Near Field Communication (NFC) enabled USB fob near to the control circuit. The data is transmitted to the USB and can then be placed into a computer where the data can be uploaded to a website where it is collated and presented, so as to facilitate better infection control in the facility in which the apparatus is installed.

Hand sanitization monitoring electronics that can be used with a selection of other hand sanitizing door handles. The hand sanitization monitoring electronics may be used on a variety of other hand sanitizing door handles which are not claimed as inventions in the present application. The logic of recording 'door opening events' and 'hand sanitization events' can be transposed to these other iterations with a minimum of changes. For example, for a latched hand sanitizing door handle, such as the technology disclosed in commonly assigned U.S. application Ser. No. 12/070,429, filed on Feb. 19, 2008; Ser. No. 12/930,607, filed on Jan. 11, 2011, Ser. No. 12/930,603, filed on Jan. 11, 2011, and U.S. Pat. No. 8,408,423, filed on Jan. 11, 2011 and issued on Apr. 2, 2013, each of which is incorporated by reference in its entirety, the 'door opening event' could be indicated by a conductive strip where the hand meets the handle. Similarly, for a hand sanitizing door handle operated by a 'push' motion, the 'door opening event' could be indicated by a change of capacitance associated with the push plate which would occur when the user pushes the door open. In both instances, the other elements of the hand sanitization monitoring electronics operates similarly, i.e., the 'hand sanitization event' would be coupled to the hand sanitization paddle, and the electronics would record and relay the data in the same way.

An ergonomically shaped trigger piece positioned at the bottom of the door handle whose contours are designed to fit the palm of the hand and invite the heel of the hand to push it (in the direction of the door) with the palm facing upward so as to receive fluid dispensed vertically from a nozzle, orifice, or opening in the trigger piece downward into the upfacing palm. By being so designed, the user pushes the heel of his hand into the trigger piece in such a manner that the sanitizing fluid will be dispensed into the palm of the hand, thereby avoiding accidental spillage. The design is such that the user will be unlikely to push the device other than with the heel of the palm. This is achieved in at least one of two ways: by ensuring that there is sufficient curvature of the trigger piece in the horizontal direction that an attempt to place a single finger or thumb is difficult because such would slip laterally by reason of there not being a sufficient flat surface for purchase and/or by requiring a degree of force which is much easier to achieve with a forward action of the palm rather than a single digit. In contrast, such is not important with the heel of the palm which is curved itself and of substantial size that there is no requirement that the user has to concentrate on making the finger or thumb contact accurately with the trigger piece.

Thus, the intuitive and natural use will be with the heel of the palm pushing the trigger piece towards the door and with the palm cupped upwards.

The apparatus does not operate, i.e., release sanitizer fluid, merely by the door being opened. Therefore, a conscious decision is required to use it, but the contrary motion of one hand holding the handle and pulling the door towards him and the other hand pushing the trigger piece toward the door is a satisfying way of arranging as the action of pulling the door toward the user will, if the other hand is held stationery by the trigger piece, result in the sanitising fluid being dispensed into the palm of the hand. The trigger piece, such as the moveable trigger wedge described below, will normally be brightly coloured and contrasted to the rest of the handle so as to draw the user's attention to it and invite the user to place the other hand there. In addition or alternatively, a logo or icon, representing the release of fluid or that of a hand with the palm facing upward, can be disposed or displayed on the trigger piece as an integral part of the trigger piece (such as, for example, by injection molding) or with, for example, a film adhered thereto. If the user uses the trigger piece to pull the door open, it will not dispense sanitising fluid. Thus, it only works if it is pushed. In general, the doors that it would be used with are not swing doors but doors where they open outwards, i.e., toward the person opening the door, as one is moving from a non-clinical environment to a more clinical environment, i.e., from hospital corridor to patient room or operating theatre. In such circumstances, it is designed to encourage people entering such environments to sanitise their hands.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
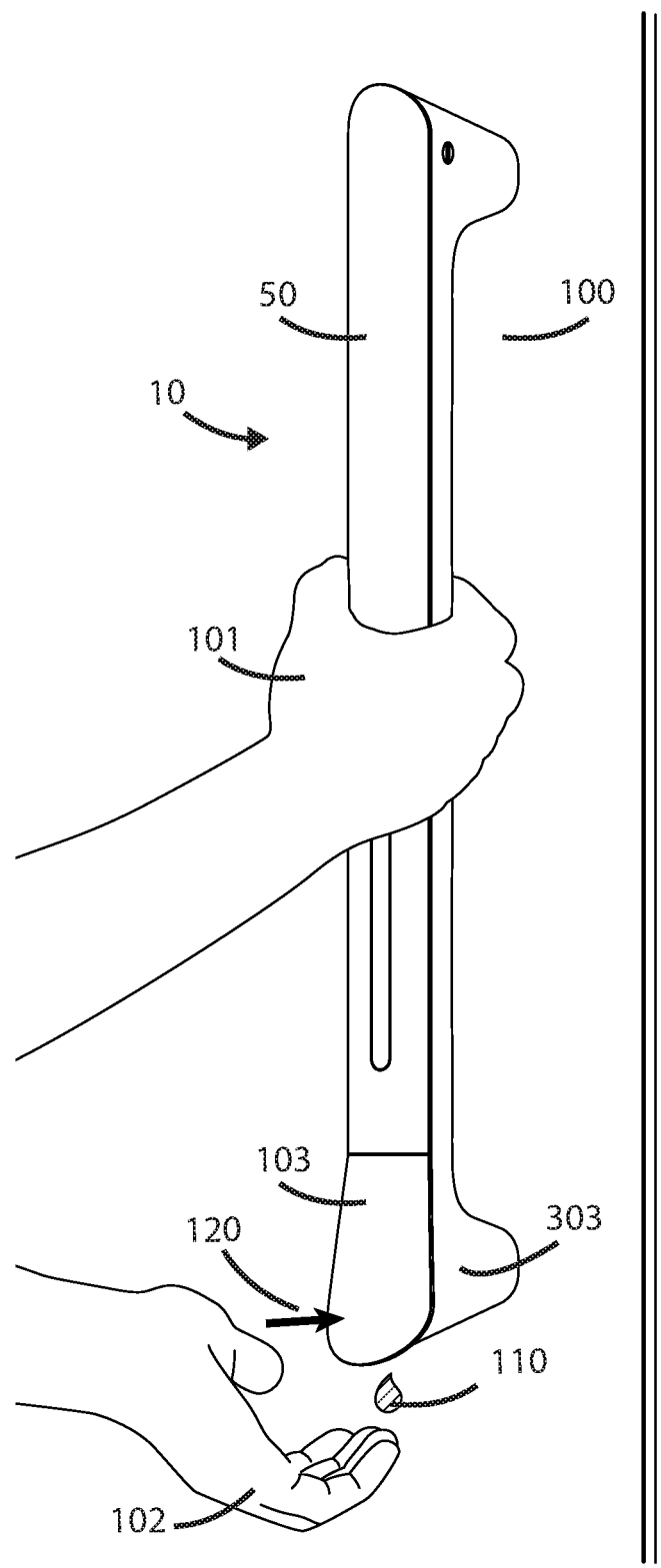
FIG. 1 depicts an isometric view of a device to promote hand sanitization being used according to at least one embodiment of the present invention.

FIG. 1 depicts an isometric view of a device 10 to promote hand sanitization being used according to at least one embodiment of the present disclosure. A door handle 50 is mounted onto, for example, a non-latched door 100, although the door 100 may be kept releasably shut by magnets, electric circuits, or other seals and door securing mechanisms as are known to those in the art. The door 100 may also comprise a latch actuated by an electric signal as are known to those in the art. The door 100 may be a door for access to, for example, operating rooms, delivery rooms, patient examination rooms, restrooms, and the like. Alternatively, the door handle 50 may be attached to equipment and medical apparatus, such as ovens, autoclaves, refrigerators, and the like. The hand 101 of a user is used to grip the door handle 50 and pull the non-latched door 100 towards the user allowing the door 100 to be opened. The user's other hand 102 can be seen under the door handle 50, near a moveable wedge trigger 103.

The shape and configuration of the moveable wedge trigger 103 is sufficiently concave in a horizontal direction to mean that an attempt to use a finger or thumb to press the moveable wedge trigger 103 is relatively much more difficult than positioning the palm of the hand 102 in an upwards direction underneath the moveable wedge trigger 103. Also, because the moveable wedge trigger 103 is positioned at the bottom of the handle 50, the palm will not be positioned in a downward facing position or in a sideways position. While the hand 102 is in this orientation, it is ideally positioned for the sanitizer fluid 110, such as an alcohol gel or foam, to be issued from a nozzle, as discussed below, into the palm of the hand as the heel of the hand depresses the moveable wedge trigger 103 in a direction 120 that is contrary to that of the hand 101. The pushing/pulling motion facilitates the dispensing of sanitizing fluid into the palm of the hand 102 and at the same time avoids spillage of the sanitizer fluid 110 onto, for example, the floor. Furthermore, the stanchion 303 of the handle 50 between the moveable wedge trigger 103 and the door handle 50 is of sufficient size and bulk that it is difficult for the hand 102 to curl around the trigger 103 in the manner set out in the figures below so as to activate the trigger with the hand positioned in the manner shown in FIG. 5 below.

Figure 2:
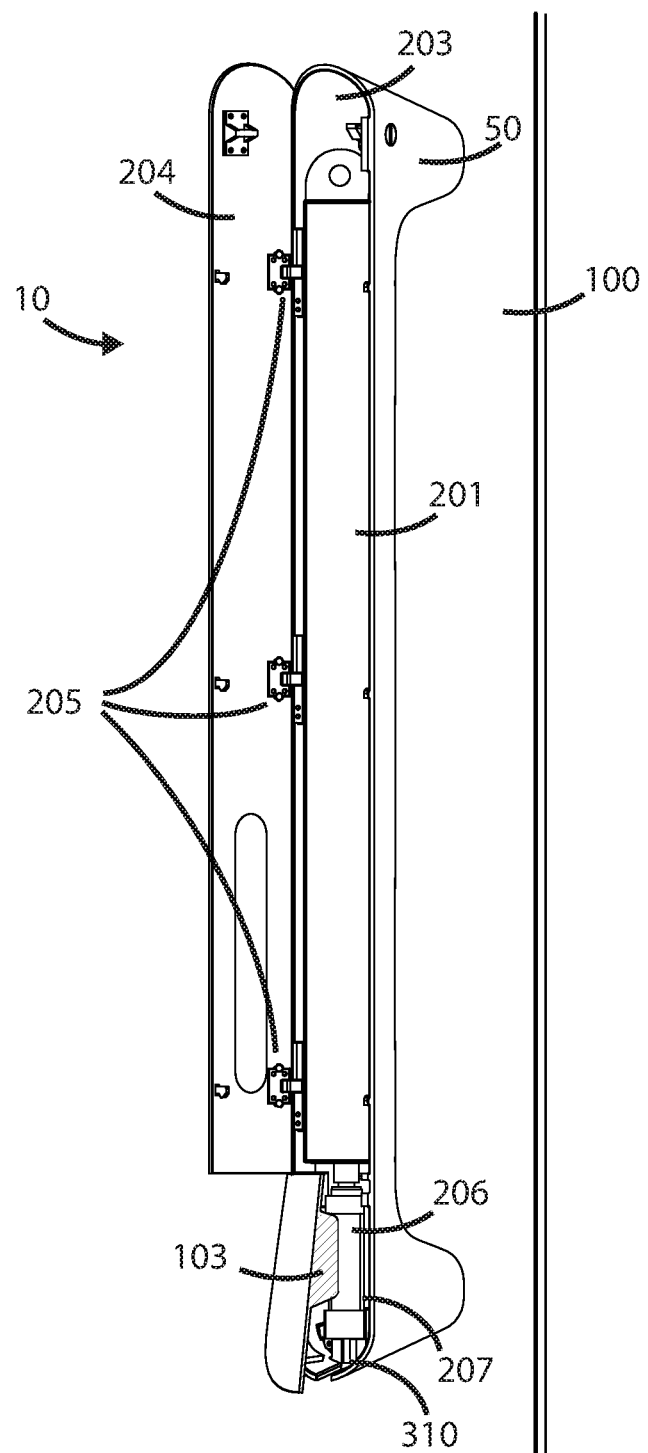
FIG. 2 depicts an isometric view of the device of FIG. 1 to promote hand sanitization being used according to embodiments of the present invention.

FIG. 2 depicts an isometric view of a device 10 of FIG. 1 to promote hand sanitization being used according to embodiments of the present invention. The device 10 can be attached to a common non-latching door 100. In some embodiments, the device 10 is attached using, for example, screws and bolts, rivets, or adhesives. A cartridge 201 containing sanitizer fluid, such as an alcohol fluid, gel or foam or other fungicidal, virucidal or biocidal agent and mixtures thereof, is slotted into the body of the doorhandle 50 by means of a front-facing door 204 which is hinged at one edge 205. The underside of the cartridge 201 features a collapsible pump 206, such as disclosed in U.S. application Ser. No. 12/918,062, which is herein incorporated by reference in its entirety, which may be made of, for example, an elastomeric material, such as natural or synthetic rubber, polybutadiene, vinyls, and/or other compliant elastomeric materials. The collapsible pump 206 is fitted to, and in fluid communication with, the cartridge 201. The collapsible pump 206 is positioned between a static wedge 207 fitted within the handle 50 and the moveable wedge trigger 103. When the moveable wedge trigger 103 is depressed by a user's hand, the collapsible pump 206 is compressed by the moveable wedge trigger 103 and the static wedge 207, causing sanitizer from the cartridge above to be transferred onto the user's hand (not pictured) from a nozzle at the terminating end of the collapsible pump 206. Also, a hand sanitization monitoring device, including speakers, LCD displays, and any related NFC transmission equipment, microcontroller, electronic memory, and the like, can be equipped and incorporated with device 10.

Figure 3:
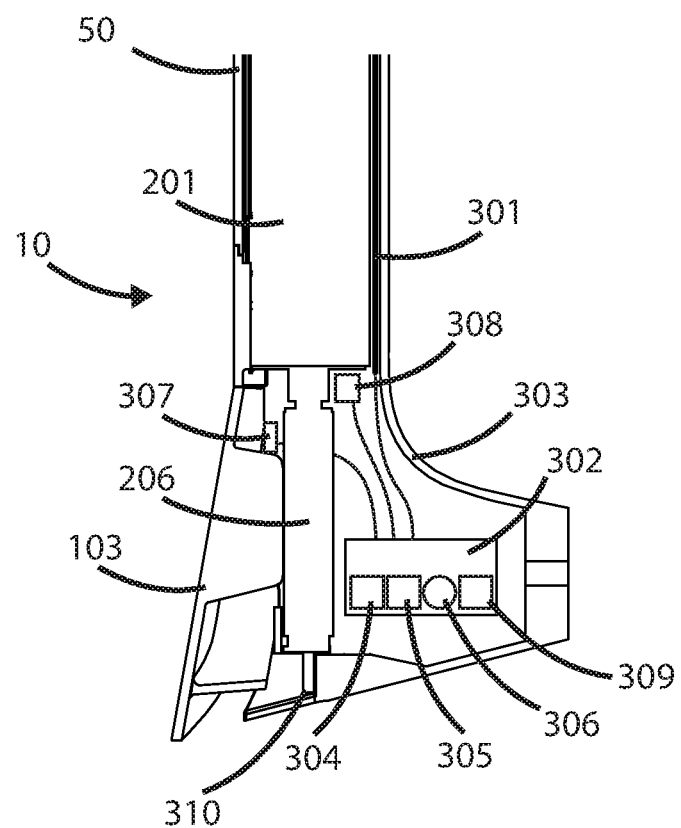
FIG. 3 depicts a partial side elevation of a device to promote hand sanitization according to embodiments of the present invention, showing a control circuit and related switches and sensing equipment.

FIG. 3 depicts a partial side elevation of the device 10 of FIG. 1 to promote hand sanitization according to embodiments of the present invention, showing a control circuit and related switches and sensing equipment. A metal strip 301 can be seen inside the device. In some embodiments, the metal strip 301 comprises, for example, aluminium, aluminium alloys, brass, stainless steel, and the like, running at least a portion of the length of the handle 50. Similarly, the metal strip may be an integral part of the handle, or the handle itself, if the handle is of any metal construction, such as described above. In some embodiments, the metal strip 301 traverses the entire length of the handle 50. The metal strip 301 is in electronic communication with a circuit board 302 positioned within the lower stanchion 303 affixing the device to the door 100 (not shown). The circuit board 302 includes electronic memory 304, and a processor 305 that is connected to a power source, such as a cell battery or alternating current sources, providing power to a system 306. Electric power is transmitted through the metal strip 301 through a wire connecting it with the circuit board 302. When the handle 50 is gripped by a hand, the system recognises a change in capacitance, and sends a signal to the processor 305, which notes a 'door opening event', which is then recorded on the electronic memory 304. In some embodiments, the device 10 is disposed on an equipment door in a horizontal position. In such embodiments, the axis of movement of the moveable wedge trigger 103 is optionally rotated by 90 degrees (not shown), so that sanitizer is issued vertically. Alternatively, the nozzle, orifice, or opening 310 (not shown), in fluid communication with the collapsible pump 206, from which sanitizer is issued may be disposed so that the sanitizer falls into the hand of a user.

The device also optionally features a 'sanitization event' switch 307, positioned on the body of the handle 50. When the moveable wedge trigger 103 is pushed, the collapsible pump 206 is compressed, delivering sanitizer fluid, gel, or foam to the hand of the user (not pictured). Subsequently, the 'sanitization event' switch 307 is activated, causing a signal to be sent to the control circuit 302 (to which it is connected by a wire), recording it as a 'sanitization event' on the memory 304. In some embodiments, the signal for the sanitization event is also sent to an electric or electronic circuit, allowing the door, whether an access door to a room or a door on a piece of equipment, to be opened by the closing or opening of a circuit. In some embodiments, the sanitization event switch 307 is not activated unless the handle 50 is gripped by a hand, whereupon the system recognises a change in capacitance as described above and a change in capacitance is sensed by the touching of a hand to moveable wedge trigger 103 and subsequently sends a signal to the processor 305. A third 'cartridge fitted' switch 308, which is connected to circuit board 302 via a wire, is depressed when a new sanitizer cartridge 201 is placed within the device and a signal is sent to the control circuit 302. When the sanitizer cartridge 201 is removed, the 'cartridge fitted' switch 308 is released and a signal is sent to the control circuit 302 indicating a 'cartridge removed' event. The precise time of each 'door opening event', 'sanitization event', 'cartridge fitted event' and 'cartridge removed event' is recorded by the control circuit 302. All data can be retrieved from the device by placing an NFC-enabled USB fob (not pictured) near to the NFC transmission section 309 of the circuit board 302. In some embodiments, data is transmitted by BlueTooth technology. In this way, any transmitted data can be collated and viewed on, for example, a computer, PC, smartphone, iPad, and other personal digital assistants (PDA), where infection prevention personnel can use the data to understand rates of hand sanitization at different times. The data can also be used to indicate when the cartridge is running low on sanitizer and also to indicate the overall rate at which sanitizer is used, targeting a date for changing the cartridge and allowing for an easier, timely resupply or ordering of sanitizer cartridges. In some embodiments of the invention, a computer or PDA, as discussed above, can send a signal to another computer to order the delivery of another cartridge from inventory so that the spent cartridge may be replaced or, alternatively, count and track cartridge usage to have a sales order placed when cartridge inventory drops below a set point.

Furthermore, in some embodiments, the sanitization switch 307 also sends a signal to the control circuit 302 that allows the door to which the handle 50 is attached to open. In other words, for an unlatched door, such as one maintained shut by an electrical or electronic circuit, by a magnet, etc., the user cannot open the door, which is an unlatched door in some embodiments, unless a sanitizing event has occurred.

Figure 4:
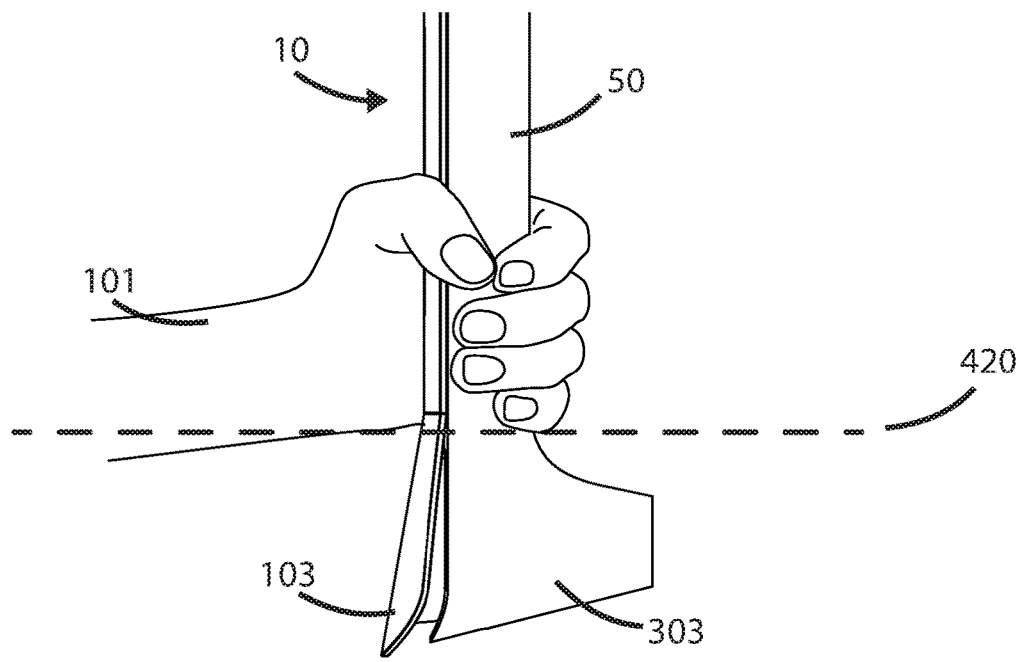
FIG. 4 depicts a side elevation of the device of FIG. 1 to promote hand sanitization according to embodiments of the present Invention, depicting a hand gripping the device.

FIG. 4 depicts a side elevation of the device 10 of FIG. 1 to promote hand sanitization according to embodiments of the present Invention, depicting the hand gripping device 10. The handle 50 is shown with a hand as near the moveable wedge trigger 103 as possible. The shape and configuration of the moveable wedge trigger 103 and the stanchion 303 is such that a user cannot, with one hand, pull the door (not shown) towards him or her and simultaneously depress the moveable wedge trigger 103. Thus, below the line 420, there the handle 50 ceases and the stanchion 303 starts. In other words, because of this design, a user cannot open the door and operate the moveable wedge trigger 103 at the same time using only one hand. Thus, the potential for improper use and spillage is greatly reduced.

Figure 5:
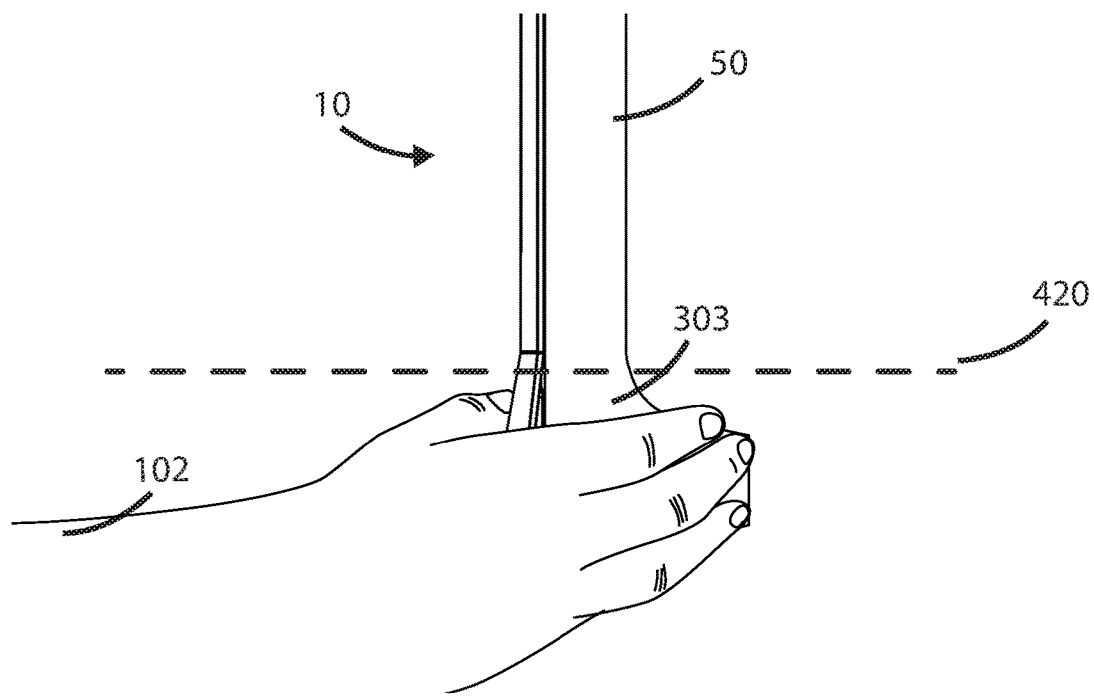
FIG. 5 depicts a side elevation of a device of FIG. 1 to promote hand sanitization according to embodiments of the present invention, showing that the user is unlikely to use the device in the manner depicted.

FIG. 5 depicts a side elevation of a device 10 of FIG. 1 to promote hand sanitization according to embodiments of the present invention, showing that the user is unlikely to use the device in the manner depicted. In other words, FIG. 5 illustrates the point discussed above. The hand, whether hand 102, or a left hand (not shown) is not able to get a good grip around the stanchion 303. The stanchion 303 prevents a closed grip of the handle below the plane formed by line 320 and thus strongly discourages the user from gripping and pulling the handle 50 in such a way that the hand is sideways onto the handle 50. Grabbing the handle 50 in such a manner would cause sanitizer fluid, for example, to be dispensed onto the floor or a countertop while the door is opened because of the awkward grip. Similarly, the lack of an ergonomic method to grip the bottom section of the handle 50 encourages the proper position of the hand (as depicted above) that is to receive the sanitizer fluid properly.

Figure 6:
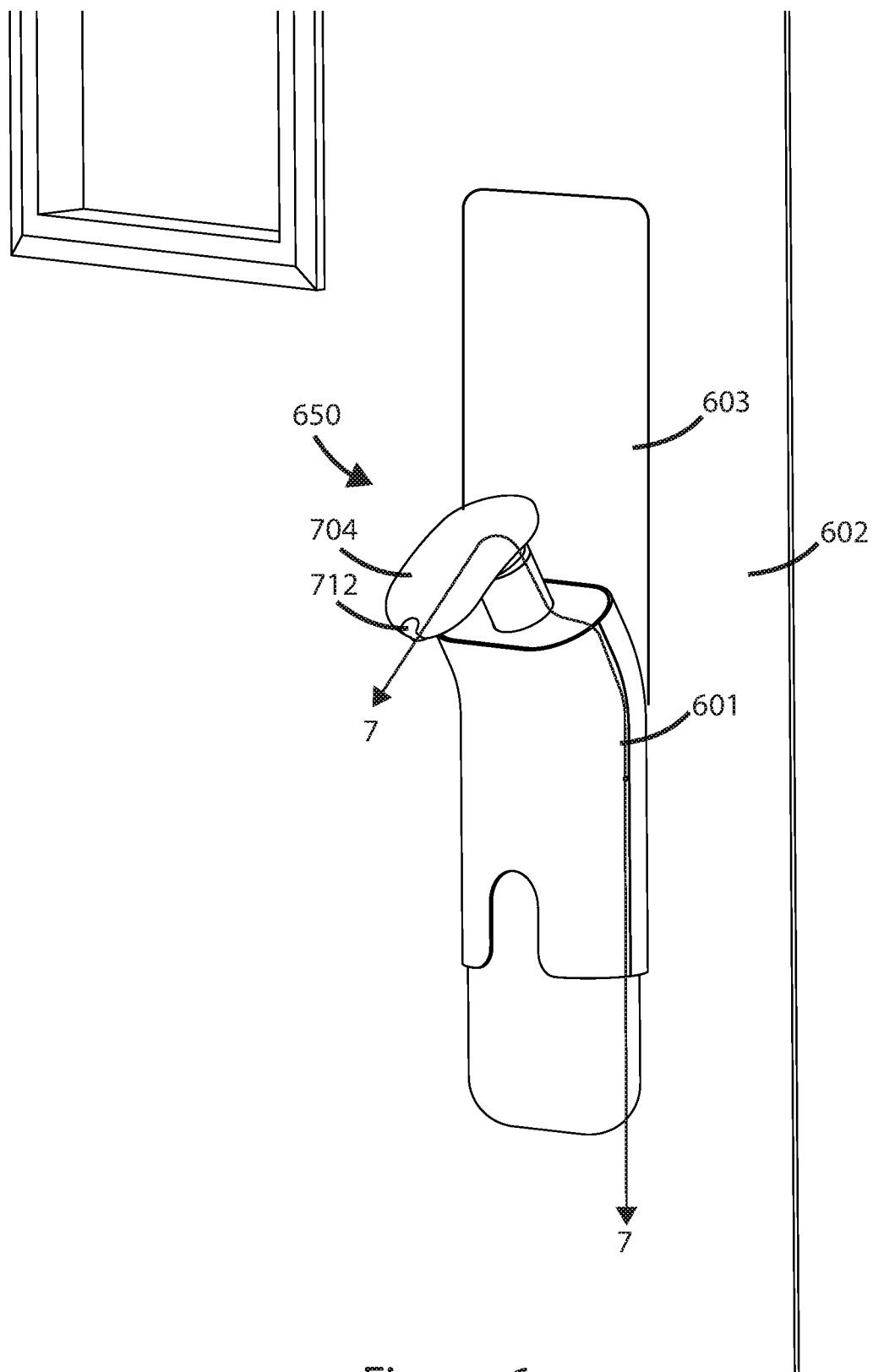
FIG. 6 depicts an isometric view of at least one embodiment of the present invention.

FIG. 6 depicts an isometric view of at least one embodiment of the present invention. FIG. 6 shows an alternative handle device 650. The device 650 is mounted to a door 602, which is in some embodiments, a latchless door as discussed above. The device 650 comprises a housing 601, which houses the components, as discussed below, and can be mounted on the door 602, which can be used to open the door 602 by a 'pushing' motion on a dispenser paddle 704, which includes a nozzle 712 at one end. The housing 601 is connected to a capacitive 'push' plate 603, (which can be made of any metal, such as, for example, aluminum or stainless steel) or other pressure sensitive devices or strain gauges as are known to those in the art that registers the presence of the hand pushing the door. In some embodiments, Hall effect sensors, which detect changes in the position of metals proximal to known magnetic fields, such as provided by a permanent magnet, are used. In some embodiments of the invention, the door 602 has the device 601 on the push side of door 602 while the pull side of the door 602 comprises a device used with a pull door, such as door 100, as discussed above.

Figure 7:
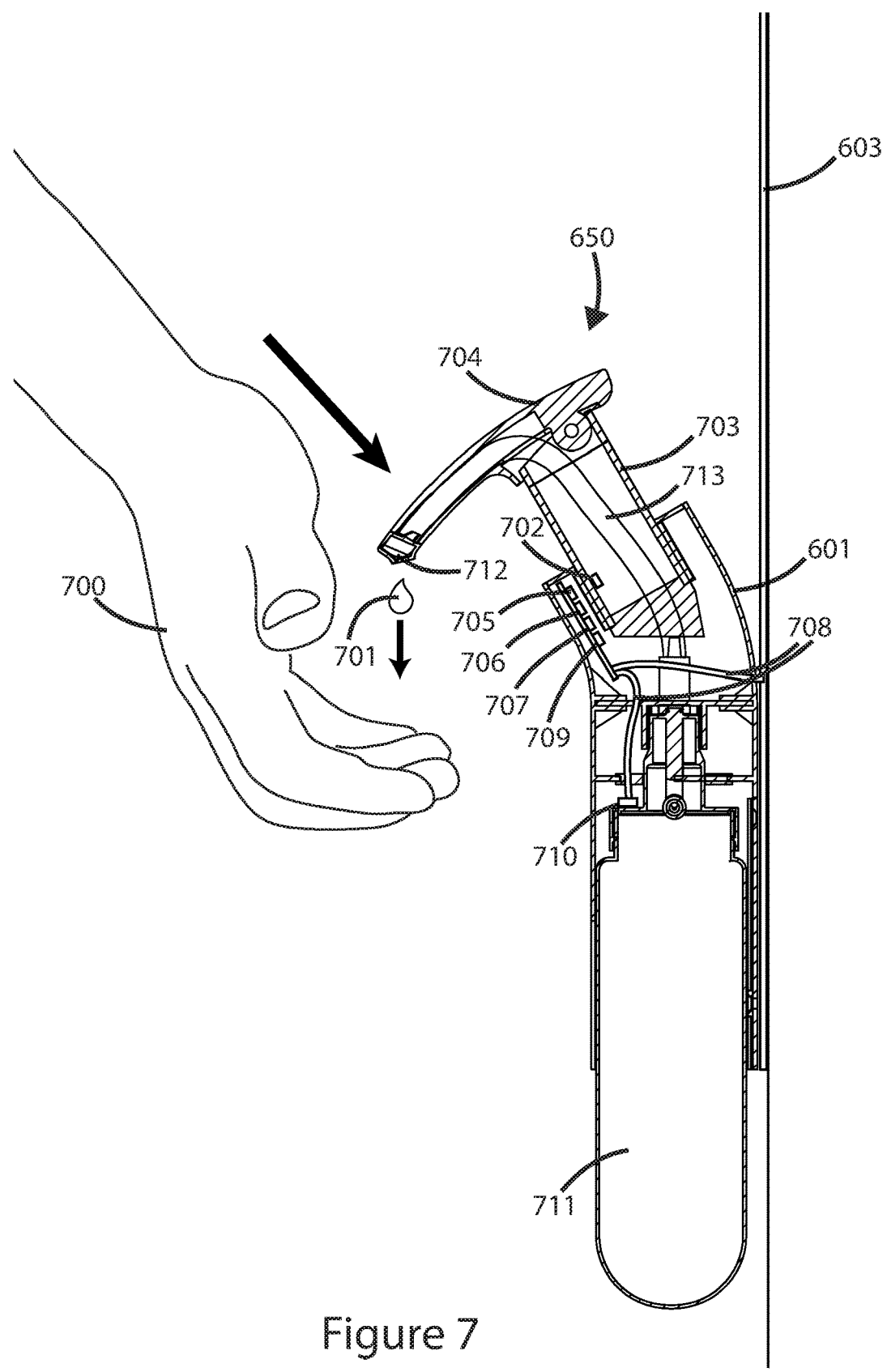
FIG. 7 depicts the section view taken along line 7-7 of FIG. 6.

FIG. 7 depicts the section view taken along line 7-7 of FIG. 6. The components comprising the sanitizing device 650 of FIG. 6 are shown. A hand 700 can also be seen operating the handle so as to provide sanitizer fluid 701 into the hand 700. A magnet 702 mounted within a bearing cylinder 703, moves in a downwards motion as a dispenser paddle 704 is depressed by the heel of the hand 700. The depression of dispenser paddle 704 causes sanitizer fluid to travel from cartridge 711, through tube 713 and nozzle 712, and onto the palm of a hand 700.

When the magnet 702 comes into range of a reed switch 705, a signal is sent to a microprocessor 706 and is recorded as a 'sanitization event' on computer memory onboard a circuit 709. When the door 602 is pushed, the capacitive plate 603 senses the presence of the hand pushing the door (not shown) and relays the signal through a wire 708 to the circuitboard 707, where it is recorded and saved as a 'door opening event'. Thereafter, the data can be relayed to an NFC device via a chip onboard the circuit 709. Similarly, a 'cartridge fitted' event is recorded when a switch 710 is depressed as a new cartridge 711 and placed into sanitizing device 750. A 'cartridge removed' event is recorded when the switch 710 is released as the empty cartridge is removed. In this way, software on a PC or PDA, as discussed above, can be used to analyse the uploaded NFC data and determine rates of hand sanitization, rates of hand sanitizer usage, and also to indicate when additional sanitizer is needed.

Figure 8:
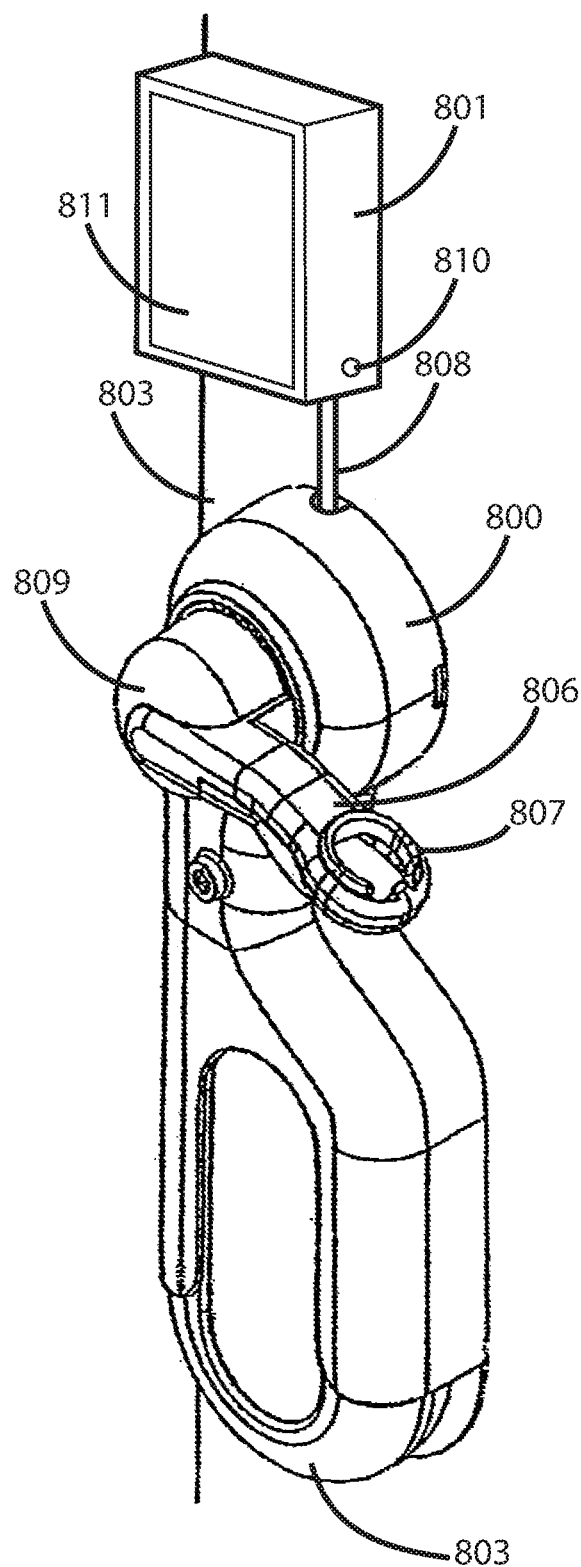
FIG. 8 depicts an isometric view of another hand sanitizing door handle in accordance with embodiments of the invention.

FIG. 8 depicts an isometric view of another hand sanitizing door handle 800 in accordance with embodiments of the invention. FIG. 8 depicts a hand sanitizing door handle 800 (as disclosed in U.S. application Ser. No. 12/930,603, which is herein incorporated by reference in its entirety, coupled to a hand sanitization monitoring device (featuring the hand sanitization monitoring electronics described above) 801 to be fitted to a standard latch mechanism of a common latching door. In embodiments of the present disclosure, the hand sanitization monitoring electronics are mounted within a separate display unit which is connected to the hand-sanitizing door handle. A cartridge 803 containing sanitizer fluid is slotted into the sanitizer agent dispensing device. When the end of the handle 806 is turned, the sanitizer trigger 807 is depressed, activating the device and delivering sanitizer to the hand via an internal spray (not pictured). When depressed by the hand, the trigger also depresses a 'sanitization event' switch inside the handle (not pictured). This switch is connected to the hand sanitization monitoring device 801 mounted above the door via a cable 808 and the internal hand sanitization monitoring circuit of this device records a 'sanitization event' when the switch is depressed. The handle section 809 is charged, such that when a hand grips the handle, a difference in capacitance is sensed and a signal is sent via the cable 808 to the hand sanitization monitoring electronics, contained within the hand sanitization monitoring device 801 where the signal is recorded as a 'door opening' event. The hand sanitization monitoring device contains a microcontroller (not pictured) and electronic memory (not pictured) which allow the door opening events to be correlated with the sanitization events, as described in the other manifestations of the hand sanitization monitoring electronics mentioned above. Similarly, the hand sanitization monitoring device 801 optionally comprises NFC transmission equipment as described above (not pictured), which can transmit this data to an external device such as a mobile phone or computer which can then further collate and present the data. The hand sanitization monitoring device 801 may also contain speakers 810 and an LCD display 811, used to issue results both visually and aurally. Also, hand sanitization monitoring device 801, including speakers 810 and LCD display 811 and any related NFC transmission equipment, microcontroller, electronic memory, and the like, can be equipped and incorporated within any other embodiment for a handle disclosed herein, such as the handles of FIGS. 2 and 7

Figure 9:
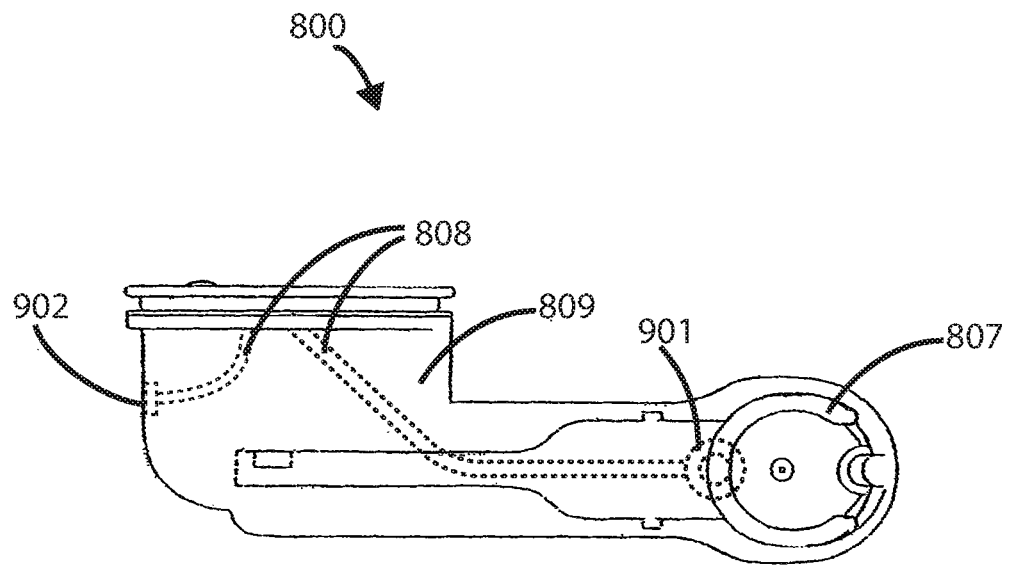
FIG. 9 depicts a top plan view of the hand sanitizing door handle of FIG. 8.

FIG. 9 depicts a top plan view of the hand sanitizing door handle of FIG. 8. FIG. 8 shows how the hand sanitization monitoring electronics interact with the hand sanitizing door handle. Hand sanitizing door handle section 809 is shown with internal details, as disclosed in commonly assigned U.S. application Ser. No. 12/930,603, fitted with the hand sanitization monitoring electronics. The sanitizer trigger 807 is positioned directly above the 'sanitization event' switch 901. When the sanitizer trigger 807 is depressed, the 'sanitization event' switch 901 is depressed, sending a signal through a cable 808 to the hand sanitization monitoring electronics (not pictured) mounted within the hand sanitization monitoring device (not pictured). A terminal 902 is used to electronically connect the handle section 809 to the hand sanitization monitoring device described above (not pictured) by the cable 808. The system detects a change in capacitance when the body of the handle 809 is gripped, which in turn, is registered as a 'door opening event'. This terminal is also connected to the hand sanitization monitoring electronics by the cable 808.

Figure 10:
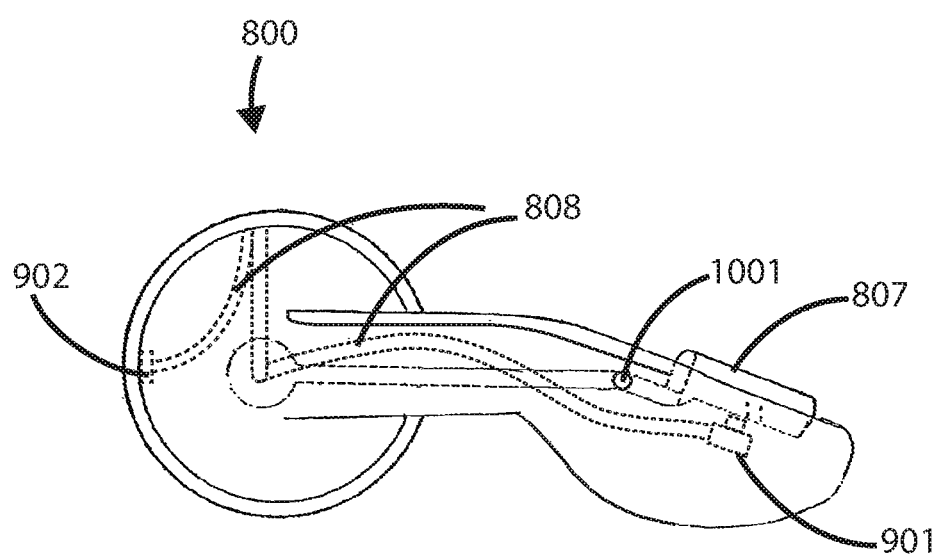
FIG. 10 depicts a side view of the handle section 809 of FIG. 8.

FIG. 10 depicts a side view of the handle section 809 of FIG. 8. The hand sanitizing door handle 800 is as disclosed in commonly assigned U.S. application Ser. No. 12/930,603), fitted with the hand sanitization monitoring electronics. The drawing shows how the hand sanitization monitoring electronics interact with the hand sanitizing door handle. The sanitizer trigger 807 rotates about a pivot point 1001 causing the sanitizer trigger switch 901 to be activated when the end of the handle is turned. The signal is sent through the cable 808 to the hand sanitization monitoring electronics (not pictured) where it is recorded as a 'hand sanitization'. By contrast, if the handle section 809 is turned without depressing the sanitizer trigger 807, the presence of the hand is causes a change in capacitance which is sensed by the hand sanitization monitoring device connected to the handle section 809 by the terminal 902 and cable 808. The hand sanitization monitoring electronics register this as a 'door opening event'. In this way, the percentage of people passing through the door and choosing to sanitize their hands by using the hand sanitizing door handle, such as the technology disclosed in commonly assigned U.S. application Ser. Nos. 12/070,429, 12/930,607, 12/930,603, and U.S. Pat. No. 8,408,423, as discussed above, can be discerned and used to monitor and improve hand sanitization interventions in hospitals and other places where infection is a problem.

While the foregoing is directed to embodiments of the present invention, other and further embodiments of the invention may be devised without departing from the basic scope thereof.

What is claimed is:

1. An apparatus for dispensing sanitizer fluid and recording data pertaining to hand sanitization, comprising:
   a sanitizer dispensing device adapted for mounting to a door;
   a cartridge disposed within the sanitizer dispensing device and adapted to contain sanitizer fluid;
   a sanitizer trigger coupled to the cartridge, and adapted to dispense said sanitizer fluid from the cartridge when activated; and
   an electronic control circuit coupled to the sanitizer trigger, wherein the electronic control circuit includes a circuit board including electronic memory and a processor connected to a power source,
   wherein the sanitizer trigger is further adapted to cause the electronic control circuit to record data pertaining to at least one recording event, and
   wherein the sanitizer dispensing device includes one of a pull door handle, push door device, or turn door handle.

2. The apparatus of claim 1, wherein the at least one recording event includes at least one of sanitizer dispensation, door opening, current level of sanitizer remaining in the cartridge, cartridge insertion, or cartridge removal.

3. The apparatus of claim 1, wherein the electronic control circuit recognises a change in capacitance and sends a signal to the processor indicating the recording event which is recorded in the electronic memory.

4. The apparatus of claim 1, further comprising a switch to indicate the presence of a sanitizer cartridge within the apparatus.

5. The apparatus of claim 1, further comprising a switch to indicate the movement of the sanitizer trigger.

6. The apparatus of claim 1, further comprising an electromechanical sensing apparatus used to sense a hand on at least one of the sanitizer dispensing device or a capacitive push plate mounted to the door.

7. The apparatus of claim 1, further comprising a control circuit and at least one of a near field communication electronic chip or a Bluetooth device.

8. The apparatus of claim 1, further comprising at least one of a speaker or a visual display.

9. The apparatus of claim 1, wherein the sanitizer dispensing device is a turn door handle adapted for mounting to the door.

10. The apparatus of claim 9, wherein turning the turn door handle causes the control circuit to transmit data pertaining to the at least one recording event.

11. The apparatus of claim 10, wherein the data or recording event is transmitted wirelessly.

12. The apparatus of claim 11, wherein the data or recording event is transmitted to at least one of a computer, a personal digital assistant, Ipad, or a smartphone.

13. The apparatus of claim 1, wherein the at least one recording event is indicated by at least one of an auditory alarm or a visual alarm.

14. The apparatus of claim 1, wherein the sanitizer dispensing device is a pull door handle adapted for mounting to the door.

15. The apparatus of claim 14, wherein pulling the pull door handle causes the control circuit to transmit data pertaining to the at least one recording event.

16. A method for dispensing sanitizer fluid from a sanitizer dispensing device mounted to a door and recording data pertaining to hand sanitization, wherein the sanitizer dispensing device includes a cartridge adapted to contain sanitizer fluid and disposed within the sanitizer dispensing device, and wherein the sanitizer dispensing device includes one of a pull door handle, push door device, or turn door handle, a sanitizer trigger coupled to the cartridge, and an electronic control circuit coupled to the sanitizer trigger, wherein the electronic control circuit includes a circuit board including electronic memory and a processor connected to a power source, the method comprising:
   recognizing a door opening event;
   recording, in the electronic memory, the door opening event;
   dispensing sanitizer fluid from the cartridge when the sanitizer trigger is activated; and
   recording, in the electronic memory, the dispensation of said sanitizer fluid as a sanitization event.

17. The method of claim 16, wherein recognizing the door opening event is determined by at least one of a change in capacitance when the sanitizer dispensing device is touched, or a change in capacitance when a capacitive push plate mounted to the door is touched, or when the door is opened.

18. The method of claim 16, wherein the door is maintained shut by at least one of an electrically actuated latch, a magnetic circuit, or an electronic circuit, and wherein a signal associated with the sanitization event is sent to the at least one electrically actuated latch, magnetic circuit, or electronic circuit allowing the door to be opened.

19. The method of claim 16, wherein the electronic control circuit further records other data including at least one of a current level of sanitizer remaining in the cartridge, a cartridge fitted event, or a cartridge removed event.

20. The method of claim 16, wherein the recorded data is transmitted to at least one of a computer, a personal digital assistant, Ipad, or a smartphone.

* * * * *